(12) United States Patent
Murakawa et al.

(10) Patent No.: US 8,606,354 B2
(45) Date of Patent: Dec. 10, 2013

(54) VISCERAL FAT MEASURING DEVICE

(75) Inventors: Yasuaki Murakawa, Kyoto (JP); Takehiro Hamaguchi, Kyoto (JP); Hiromichi Karo, Kyoto (JP); Tomoya Ijiri, Kameoka (JP); Shojiro Oku, Kyoto (JP)

(73) Assignee: Omron Healthcare Co., Ltd., Kyoto-Shi (JP)

( * ) Notice: Subject to any disclaimer, the term of this patent is extended or adjusted under 35 U.S.C. 154(b) by 103 days.

(21) Appl. No.: 13/009,608

(22) Filed: Jan. 19, 2011

(65) Prior Publication Data
US 2011/0130676 A1   Jun. 2, 2011

Related U.S. Application Data

(63) Continuation of application No. PCT/JP2009/064446, filed on Aug. 18, 2009.

(30) Foreign Application Priority Data

Sep. 22, 2008   (JP) ................................. 2008-242626

(51) Int. Cl.
*A61B 5/05*   (2006.01)

(52) U.S. Cl.
USPC .......................................................... 600/547

(58) Field of Classification Search
USPC ............................................ 600/547; 24/309
See application file for complete search history.

(56) References Cited

U.S. PATENT DOCUMENTS

| 1,738,900 | A | * | 12/1929 | Henry | ............................. 24/309 |
| 2004/0077969 | A1 | | 4/2004 | Onda et al. | |
| 2005/0107717 | A1 | | 5/2005 | Yamamoto et al. | |
| 2007/0038092 | A1 | * | 2/2007 | Jean-Claude et al. | ......... 600/438 |
| 2007/0175007 | A1 | * | 8/2007 | Chan | ............................... 24/614 |
| 2009/0084674 | A1 | | 4/2009 | Holzhacker et al. | |

FOREIGN PATENT DOCUMENTS

| CN | 1602804 A | 4/2005 |
| EP | 1935338 A1 * | 6/2008 |
| JP | A 11-113870 | 4/1999 |
| JP | A 2002-369806 | 12/2002 |
| JP | A 2006-34598 | 2/2006 |
| JP | A 2007-130072 | 5/2007 |
| JP | A 2007-222685 | 9/2007 |
| WO | WO 2007/043271 A1 | 4/2007 |
| WO | WO 2007/070997 A1 | 6/2007 |

OTHER PUBLICATIONS

International Search Report issued in PCT/JP2009/064446, mailed Sep. 29, 2009. (with English-language translation).
Nov. 29, 2012 Office Action issued in Chinese Patent Application No. 200980132817.1 (with English translation).

* cited by examiner

*Primary Examiner* — Brian Szmal
*Assistant Examiner* — Megan Leedy
(74) *Attorney, Agent, or Firm* — Oliff & Berridge, PLC

(57) ABSTRACT

A visceral fat measuring device is capable of simply and noninvasively measuring a visceral fat amount, by calculating the visceral fat amount based on trunk measurement information, impedance information of the entire trunk, and impedance information of a surface layer of the trunk. The visceral fat measuring device includes: a belt to be wound around the trunk that has a pressing member with electrodes E to be pressed onto the dorsal side of a person subjected to measurement; a pair of belt portions respectively fixed to both sides of the pressing member; a buckle for connecting the pair of belt portions; and indicators on the pair of belt portions to show distances from a reference position of the belt.

15 Claims, 12 Drawing Sheets

VISCERAL FAT MEASURING DEVICE

This is a Continuation of Application No. PCT/JP2009/064446 filed Aug. 18, 2009, which claims the benefit of Japanese Patent Application No. 2008-242626, filed Sep. 22, 2008. The disclosure of the prior application is hereby incorporated by reference herein in its entirety.

TECHNICAL FIELD

The present invention relates to a visceral fat measuring device.

BACKGROUND ART

Conventionally, there is a known method of measuring a visceral fat amount from a tomographic image taken with using X ray CT and MRI. According to such a measuring method, although the visceral fat amount can be measured with high precision, large-sized facilities are required. Thus, measurement is only performed in medical treatment facilities where the X ray CT and the MRI are installed. Therefore, daily measurement of the visceral fat amount by such a measuring method is not realistic. It should be noted that although the X ray CT is capable of taking a finer image than the MRI, there is a known risk of radiation exposure.

Realization of a device capable of simply and noninvasively measuring the visceral fat amount is desired.

It should be noted that a related technology is disclosed in patent document 1.

RELATED ART DOCUMENT

Patent Document

Patent Document 1: Japanese Unexamined Patent Publication No. 2002-369806

DISCLOSURE OF THE INVENTION

Problems to be Solved by the Invention

An object of the present invention is to provide a visceral fat measuring device capable of simply and noninvasively measuring a visceral fat amount.

Means for Solving the Problem

In the present invention, the following means are adopted in order to solve the above problem.

That is, in a visceral fat measuring device of the present invention for calculating a visceral fat amount based on trunk measurement information serving as a basis for calculating a trunk sectional area in a section on an abdominal part of a trunk which is orthogonal to a body axis of the trunk, impedance information of the entire trunk obtained by applying an electric current from hands and legs to the trunk and measuring a potential difference in part of a surface of the trunk, and impedance information of a surface layer of the trunk obtained by winding a belt having a plurality of electrodes around the trunk so as to apply the electric current through the vicinity of the surface layer of the trunk and measure a potential difference in part of the surface of the trunk, the belt includes a pressing member pressed onto the dorsal of a person subjected to measurement and provided with the electrodes, a pair of belt portions respectively fixed to the both sides of the pressing member, and a buckle for fixing a pair of the belt portions, and indicators (such as scale markings, numerical values, characters, symbols, pictures, and combination of not less than two of the above indicators) showing distances from a reference position of the belt (such as fixing positions of the belt portions to the pressing member and a center position in the width direction of the pressing member) are respectively provided in a pair of the belt portions.

It should be noted that the visceral fat amount in the present invention includes indicators showing the visceral fat amount such as a visceral fat sectional area, a visceral fat volume, and a ratio of the visceral fat sectional area relative to an abdominal sectional area.

According to the present invention, the visceral fat amount can be measured from the trunk measurement information serving as the basis for calculating the trunk sectional area, the impedance information of the entire trunk, and the impedance information of the surface layer of the trunk. A circumferential length of a waist part (waist length) or vertical width and horizontal width of the trunk are taken as the trunk measurement information serving as the basis for calculating the trunk sectional area, and these can be easily measured. Since the impedance information can be obtained by measuring the potential difference in a state that an electric current is applied to a human body (a living body), the impedance information can be also easily obtained. Therefore, the visceral fat amount can be relatively easily and noninvasively measured.

In the present invention, by winding the belt around the trunk so that the pressing member provided with the electrodes is pressed onto the dorsal of the person subjected to the measurement, the electrodes are brought into contact with predetermined positions. Therefore, there is a concern that the electrodes are not easily matched with the predetermined positions. However, in the present invention, the indicators showing the distances from the reference position are respectively provided in a pair of the belt portions. Therefore, by winding the belt around a waist while seeing the indicators, a position of the pressing member (that is, positions of the electrodes) can be easily adjusted.

In a case where the potential difference in part of the surface of the trunk is measured, a potential difference on the dorsal side may be measured.

In a case where the potential difference in part of the surface of the trunk is measured, a potential difference in the body axis direction of the trunk may be measured.

The buckle may be provided with a pair of rollers around which a pair of the belt portions is respectively wound, the rollers for respectively supporting a pair of the belt portions.

In such a way, since members for supporting the belt portions are formed by the rollers, movement of the belt portions relative to the buckle is smoothed, so that a position adjustment task of the pressing member can be smoothly performed.

A transparent plate may be provided in a center of the buckle, and an indicator showing a center in the width direction of the buckle may be provided in this transparent plate.

Thereby, position matching of the buckle with a center of the abdominal part can be easily performed. With a synergetic effect with the indicators provided in the belt portions, the position of the pressing member (that is, the positions of the electrodes) can be more easily adjusted.

An indicator showing a center position in the width direction of the pressing member may be provided on a back surface of a surface of the pressing member to be pressed onto the dorsal.

In such a way, in a case where a third person other than the person subjected to the measurement presses the pressing member onto the dorsal of the person subjected to the measurement, the position matching of the pressing member can be easily performed.

A lean body sectional area excluding a fat may be calculated from the impedance information of the entire trunk, a subcutaneous fat sectional area may be calculated from the impedance information of the surface layer of the trunk, and a visceral fat sectional area may be calculated by subtracting the lean body sectional area and the subcutaneous fat sectional area from the trunk sectional area calculated from the trunk measurement information.

That is, the impedance of the entire trunk is largely influenced by an amount of lean body (viscera, muscles, and skeletons) excluding the fat. The lean body sectional area can be calculated from this impedance. The impedance of the surface layer of the trunk is largely influenced by an amount of a subcutaneous fat amount. The subcutaneous fat sectional area can be calculated from this impedance. It should be noted that a subcutaneous fat is generally accumulated in an area from sides to the dorsal side rather than the abdominal side of the trunk. Thus, by measuring the impedance on the dorsal side, the subcutaneous fat sectional area can be more precisely measured. With using the lean body sectional area and the subcutaneous fat sectional area obtained in such a way, by subtracting these areas from the trunk sectional area, the visceral fat sectional area can be obtained.

It should be noted that the above configurations can be combined and adopted as far as possible.

Effect of the Invention

As described above, according to the present invention, the visceral fat amount can be simply and noninvasively measured.

BEST MODE FOR CARRYING OUT THE INVENTION

Modes for carrying out this invention will be described in detail as examples with reference to the drawings based on an embodiment. However, the scope of this invention is not limited to size, materials, shapes, relative arrangement, and the like of constituent elements described in this embodiment unless specifically described.

EMBODIMENT

With reference to FIGS. 1 to 12, a visceral fat measuring device according to the embodiment of the present invention will be described.
(Measurement Principle of Visceral Fat)

Figure 1:
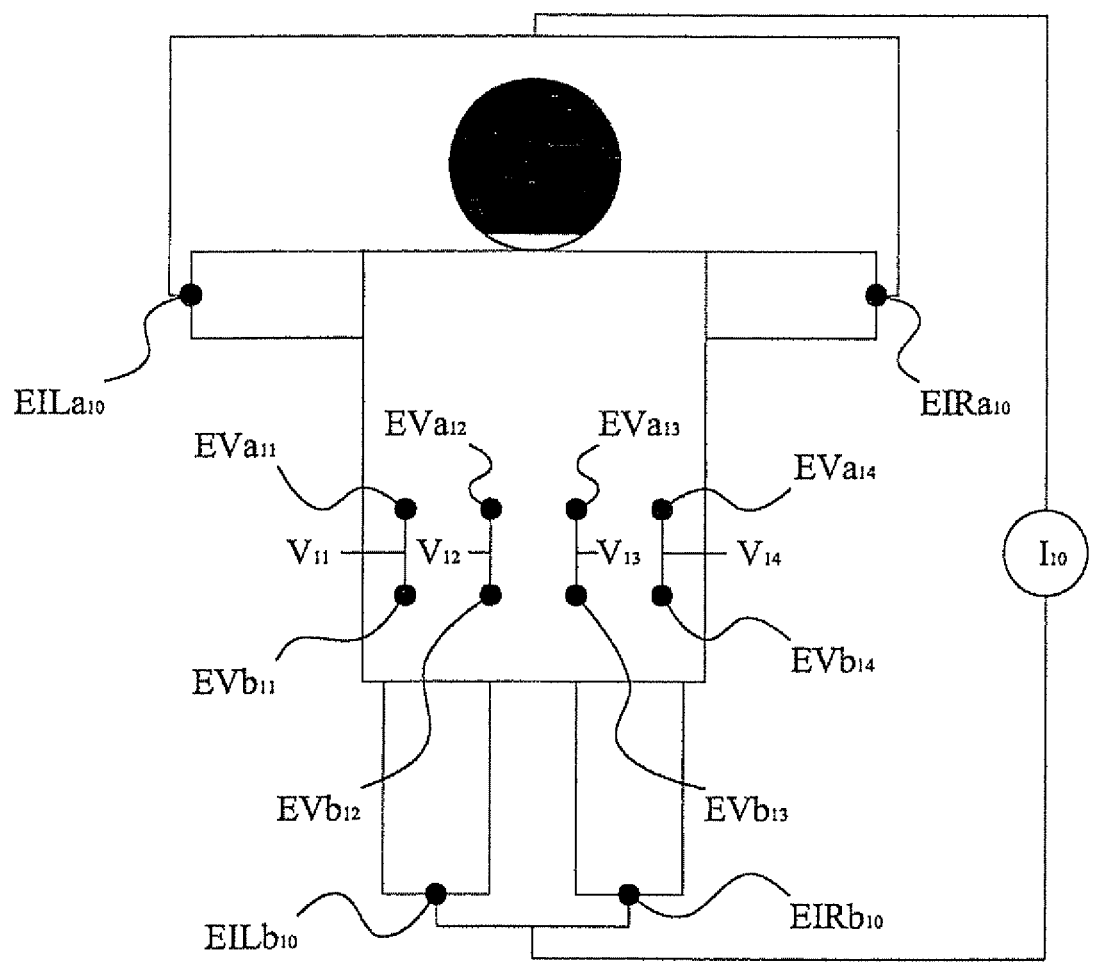
FIG. 1 is a schematic view showing a state when impedance is measured.
Figure 2:
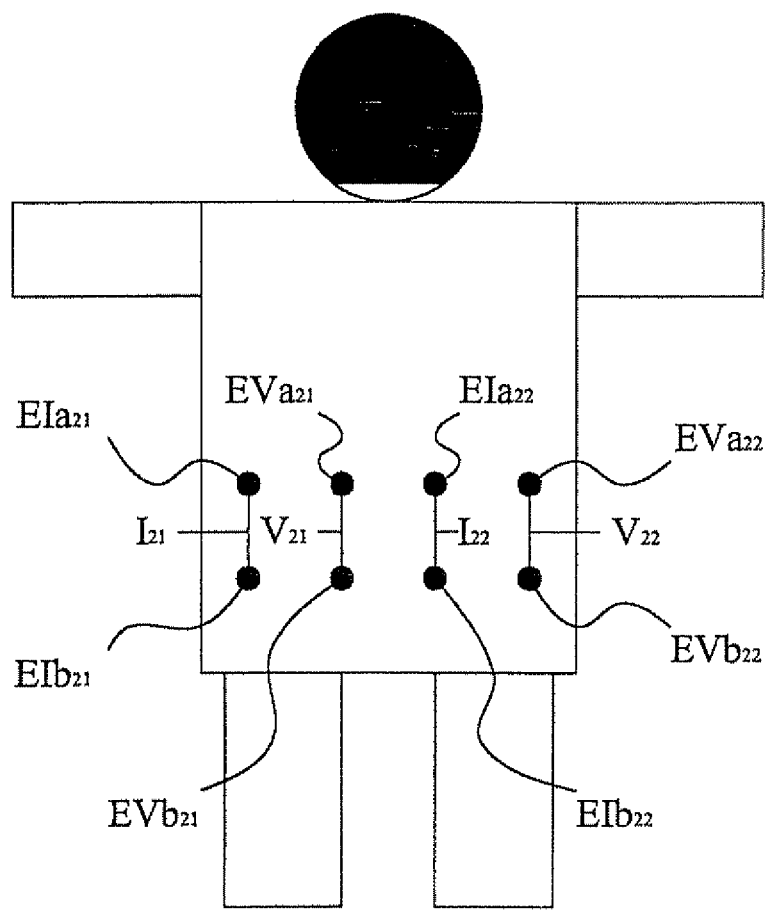
FIG. 2 is a schematic view showing a state when impedance is measured.

With reference to FIGS. 1 and 2, a measurement principle of a visceral fat in the visceral fat measuring device according to the embodiment of the present invention will be described. FIGS. 1 and 2 are schematic views showing states when impedance is measured. It should be noted that FIGS. 1 and 2 show states seen from the dorsal side of a user subjected to measurement of the visceral fat.

FIG. 1 shows the state in a case where impedance information of the entire trunk is obtained. As shown in the figure, electrodes EILa10, EIRa10 are respectively attached to both hands of the user subjected to the measurement of the visceral fat. Electrodes EILb10, EIRb10 are also respectively attached to both legs of the user. Pairs of electrodes provided side by side in the body axis direction of the trunk are attached at four points in the horizontal width direction of the trunk on the dorsal side of the trunk of the user. That is, the total of eight electrodes EVa11, EVb11, EVa12, EVb12, EVa13, EVb13, EVa14, EVb14 are attached.

In this state, an electric current I10 passing through the trunk is applied with using the electrodes EILa10, EIRa10, EILb10, EIRb10 respectively attached to the both hands and the both legs. A potential difference V11 is measured with using a pair of the electrodes EVa11, EVb11, a potential difference V12 is measured with using a pair of the electrodes EVa12, EVb12, a potential difference V13 is measured with using a pair of the electrodes EVa13, EVb13, and a potential difference V14 is measured with using a pair of the electrodes EVa14, EVb14. That is, the potential differences in part of a surface of the trunk are measured at the four points on the dorsal side.

Impedance Zt of the entire trunk is calculated from the potential differences measured in such a way. It should be noted that by measuring the potential differences V11, V12, V13, V14 at the four points and calculating the impedance of the entire trunk with using an average value thereof, an influence of varied fat distribution in the trunk, and the like can be reduced.

In a case where the electric current I10 is applied from the both hands and the both legs which are distant from the trunk, almost all the electric current I10 passes through a part where electric resistance is low, that is, a part other than a fat. Therefore, the impedance Zt of the entire trunk calculated from the potential differences V11, V12, V13, V14 measured with using such an electric current I10 is largely influenced by an amount of lean body (viscera, muscles, and skeletons) excluding the fat. Therefore, a lean body sectional area Sa (estimated value) can be calculated from this impedance Zt.

FIG. 2 shows the state in a case where impedance information of a surface layer of the trunk on the dorsal side of the trunk is obtained. As shown in the figure, pairs of electrodes provided side by side in the body axis direction of the trunk are attached at four points in the horizontal width direction of the trunk on the dorsal side of the trunk of the user. That is, the total of eight electrodes EIa21, EIb21, EVa21, EVb21, EIa22, EIb22, EVa22, EVb22 are attached.

In this state, an electric current I21 is applied with using a pair of the electrodes EIa21, EIb21, and an electric current I22 is applied with using a pair of the electrodes EIa22, EIb22. It should be noted that a current value of the electric current I21 and a current value of the electric current I22 are the same. A potential difference V21 is measured with using a pair of the electrodes EVa21, EVb21, and a potential difference V22 is measured with using a pair of the electrodes EVa22, Evb22. That is, the potential differences in part of the surface of the trunk are measured at the two points on the dorsal side.

Impedance Zs of the surface layer on the dorsal side of the trunk is calculated from the potential differences measured in such a way. It should be noted that by measuring the potential differences V21, V22 at the two points and calculating the impedance Zs of the surface layer of the trunk with using an average value thereof, an influence of varied subcutaneous fat and the like can be reduced. It should be noted that by switching a circuit so that the electrodes for applying the electric current serve as electrodes for measuring the potential differences, and the electrodes for measuring the potential differences serve as electrodes for applying the electric currents, the potential differences can be measured at the four points. In such a way, the influence of the varied subcutaneous fat and the like can be furthermore reduced.

In a case where the electric currents I21, I22 are applied by a pair of the electrodes attached at the positions on the back side of an abdominal part on the dorsal, almost all the electric currents I21, I22 pass through the surface layer of the trunk. Therefore, the impedance Zs of the surface layer of the trunk calculated from the potential differences V21, V22 measured with using such electric currents I21, I22 is largely influenced by an amount of a subcutaneous fat amount. Therefore, a subcutaneous fat sectional area Sb (estimated value) can be calculated from this impedance Zs.

Therefore, when a trunk sectional area (an area of a section on the abdominal part of the trunk which is orthogonal to a body axis of the trunk) is St, a visceral fat sectional area Sx is Sx=St−Sa−Sb. Thus, the visceral fat sectional area Sx can be calculated.

The trunk sectional area St can be calculated from a circumferential length of a waist part (waist length) or vertical width and horizontal width of the trunk (in the vicinity of the abdominal part). For example, in a case of calculating from the vertical width and the horizontal width of the trunk, when the horizontal width of the trunk is 2a, and the vertical width is 2b, the section of the trunk is substantially oval. Thus, the trunk sectional area is substantially $\pi \times a \times b$. However, this value is highly susceptible to an error. Thus, by multiplying a coefficient for correcting the error, a more precise trunk sectional area St can be obtained. With regard to this coefficient, for example based on a large number of X ray CT image samples, an optical value of α can be determined from a relationship between a trunk sectional area St' obtained from the X ray CT images, and a value a, and a value b so as to satisfy St'=α×π×a×b.

Thereby, based on the horizontal width 2a and the vertical width 2b of the trunk, the trunk sectional area St (=α×π×a×b) with less error can be calculated. It should be noted that since the value α multiplied for correction may have an optimal value appropriately differentiated in accordance with gender, age, body height, weight, and the like (hereinafter, these are called as user information), by changing the value α in accordance with the user subjected to the measurement, the more precise trunk sectional area St can be calculated.

As described above, the lean body sectional area Sa can be calculated from the impedance Zt of the entire trunk. However, the lean body sectional area Sa cannot be calculated only with the impedance Zt of the entire trunk. That is, there is a need for converting a value proportional to size of the trunk obtained from the impedance Zt into the lean body sectional area Sa. More specifically, for example, the lean body sectional area Sa can be expressed as Sa=β×a×(1/Zt).

The value a is a half of the horizontal width of the trunk as described above, which is a value relating to the size of the trunk. This value is not limited to this. For example, (a×b) may be used so that values of the vertical width and the horizontal width of the trunk are reflected, the trunk sectional area St may be used, or the circumferential length of the waist part (the waist length) may be used.

The value β is a coefficient for converting into the lean body sectional area Sa, and an optimal value thereof can be determined from a large number of the X ray CT image samples as well as a case where the value α is determined. That is, based on a large number of the X ray CT image samples, the optimal value of β can be determined from a relationship between a lean body sectional area Sa' obtained from the X ray CT images, and the value a, and the impedance Zt of the entire trunk of a person subjected to the X ray CT images so as to satisfy Sa'=β×a(1/Zt).

Further, as described above, the subcutaneous fat sectional area Sb can be calculated from the impedance Zs of the surface layer of the trunk on the back side of the abdominal part on the dorsal. However, the subcutaneous fat sectional area Sb cannot be calculated only with the impedance Zs of the surface layer. That is, there is a need for converting a value proportional to the size of the trunk obtained from the impedance Zs into the subcutaneous fat sectional area Sb. More specifically, the subcutaneous fat sectional area Sb can be expressed as Sb=γ×a×Zs.

The value a is the half of the horizontal width of the trunk as described above, which is the value relating to the size of the trunk. This value is not limited to this. For example, (a×b) may be used so that the values of the vertical width and the horizontal width of the trunk are reflected, the trunk sectional area St may be used, or the circumferential length of the waist part (the waist length) may be used.

The value γ is a coefficient for converting into the subcutaneous fat sectional area Sb, and an optimal value thereof can be determined from a large number of the X ray CT image samples as well as a case where the value α is determined. That is, based on a large number of the X ray CT image samples, the optimal value of γ can be determined from a relationship between a subcutaneous fat sectional area Sb' obtained from the X ray CT images, and the value a, and the impedance Zs of the surface layer of the trunk of the person subjected to the X ray CT images so as to satisfy Sb'=γ×a×Zs.

It should be noted that the above values β and γ may have optical values appropriately differentiated in accordance with the user information as well as the value α used in a case where the sectional area of the abdominal part is determined. Therefore, by changing the values β and γ in accordance with the user subjected to the measurement, more precise lean body sectional area Sa and subcutaneous fat sectional area Sb can be calculated.

As described above, in the visceral fat measuring device according to the present embodiment, the visceral fat sectional area Sx is calculated from the trunk sectional area St, the lean body sectional area Sa calculated based on the impedance Zt of the entire trunk, and the subcutaneous fat sectional area Sb calculated based on the impedance Zs of the surface layer of the trunk.

That is, the visceral fat sectional area is expressed as Sx=St−Sa−Sb.

In this case, St=α×π×a×b, Sa=β×a×(1/Zt), and Sb=γ×a×Zs are established. Then, the value a is the half of the horizontal width of the trunk, and the value b is a half of the vertical width of the trunk. The values α, β, γ are the coefficients obtained based on a large number of the X ray CT image samples for determining the optimal values of St, Sa, Sb. It should be noted that these coefficients can be changed in accordance with the user information as described above.

As clear from the above expression, the measured (calculated) visceral fat amount is the visceral fat sectional area. However, the visceral fat amount as a measurement result is not limited to the visceral fat sectional area but may be a ratio of the visceral fat sectional area relative to the trunk sectional area, or a visceral fat volume converted from the visceral fat sectional area.

It should be noted that as clear from the above expression, the measurement principle of the visceral fat in the visceral fat measuring device according to the embodiment of the present invention is based on a thought that the visceral fat sectional area Sx can be obtained by subtracting the lean body sectional area Sa and the subcutaneous fat sectional area Sb from the trunk sectional area St.

However, the visceral fat measuring device according to the present invention is not always limited to simple adoption of the above expression Sx=St−Sa−Sb, but also includes application of such a principle.

For example, the visceral fat sectional area Sx can be determined from Sx=St−Sa−Sb+δ (δ is a correction amount). That is, with similar methods to a case where the above values α, β, γ are determined, the correction amount δ can be added based on a large number of the X ray CT image samples.

The visceral fat sectional area Sx can be determined from Sx=St−F (Zt, Zs, a, b). It should be noted that F (Zt, Zs, a, b) is a function having Zt, Zs, a, b as parameters.

That is, a total value of the lean body sectional area Sa and the subcutaneous fat sectional area Sb has a correlation with the impedance Zt of the entire trunk, the impedance Zs of the surface layer of the trunk, and the size of the trunk (the vertical width and the horizontal width of the trunk in the present embodiment). Therefore, the total value of the lean body sectional area Sa and the subcutaneous fat sectional area Sb can be determined from the function F (Zt, Zs, a, b) having the values Zt, Zs, a, b as the parameters. It should be noted that this function F (Zt, Zs, a, b) can also be derived from a large number of the X ray CT image samples.

(Entire Configuration of Visceral Fat Measuring Device)

Figure 3:
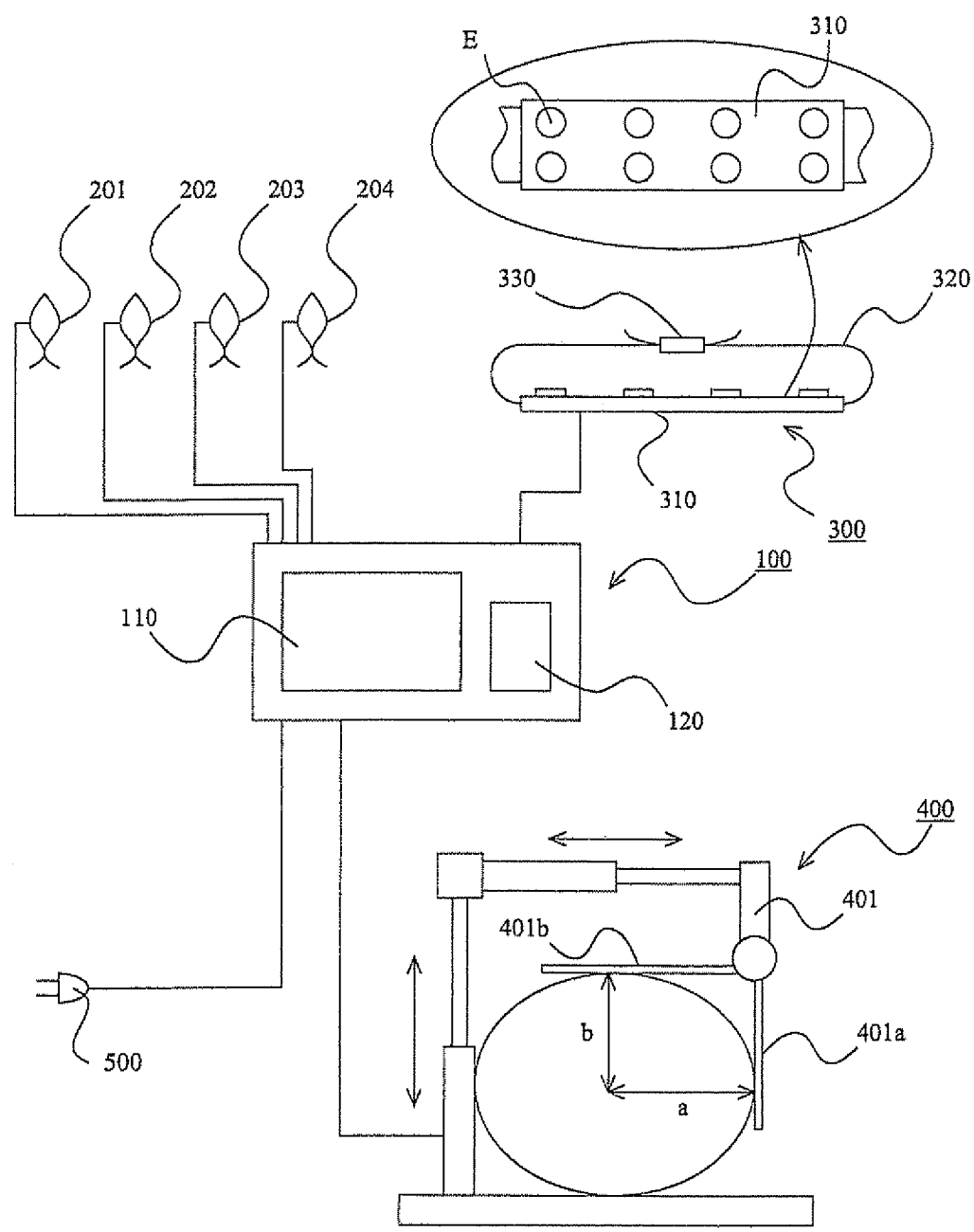
FIG. 3 is an entire configuration diagram of a visceral fat measuring device according to an embodiment of the present invention.

The entire configuration of the visceral fat measuring device according to the present embodiment will be described with reference to FIG. 3. FIG. 3 is an entire configuration diagram of the visceral fat measuring device according to the embodiment of the present invention.

The visceral fat measuring device according to the present embodiment is provided with a device main body 100, four clips 201, 202, 203, 204 for attaching electrodes to the hands and the legs, a belt 300 for attaching electrodes to the dorsal, a measuring unit 400 for measuring the vertical width and the horizontal width of the trunk, and a socket 500 for supplying electric power to the device main body 100.

The device main body 100 is provided with a display unit 110 for displaying various input information and the measurement result, and an operation unit 120 for turning on or off a power supply of the device main body 100 and inputting the various information.

The clips 201, 202, 203, 204 are respectively provided with the electrodes. By attaching these clips 201, 202, 203, 204 to the hands and the legs (preferably, wrists and ankles) so as to nip the hands and the legs, the electrodes can be closely attached to the hands and the legs. It should be noted that the electrodes respectively provided in the clips 201, 202, 203, 204 correspond to the electrodes EILa10, EIRa10, EILb10, EIRb10 shown in FIG. 1.

The belt 300 is provided with a pressing member 310 to be pressed onto the dorsal of the user subjected to the measurement, belt portions 320 respectively fixed to the both sides of the pressing member 310, and a buckle 330 for fixing the belt portions 320. The total of eight electrodes E are provided in the pressing member 310. By winding the belt 300 formed in such a way around a waist so that the pressing member 310 is abutted against a slightly upper part of coccyx, the eight electrodes E can be closely attached at positions on the back side of the abdominal part on the dorsal of the user. It should be noted that these eight electrodes E correspond to the eight electrodes EVa11, EVb11, EVa12, EVb12, EVa13, EVb13, EVa14, EVb14 shown in FIG. 1, and the eight electrodes EIa21, EIb21, EVa21, EVb21, EIa22, EIb22, EVa22, Evb22 shown in FIG. 2. That is, by switching the electric circuit in the device main body 100 between a case where the impedance Zt of the entire trunk is calculated and a case where the impedance Zs of the surface layer of the trunk is calculated, roles of the eight electrodes E can be changed.

The measuring unit 400 includes a cursor support portion 401 provided with a horizontal width measuring cursor portion 401a and a vertical width measuring cursor portion 401b. This cursor support portion 401 is formed to be movable in the up and down direction and the left and right direction. With using this measuring unit 400, for example, by moving the cursor support portion 401 to positions where the horizontal width measuring cursor portion 401a and the vertical width measuring cursor portion 401b are respectively brought into contact with sides and a navel and a periphery thereof in a state that the user lies on a bed, the horizontal width 2a and the vertical width 2b can be measured. It should be noted that in the present embodiment, the horizontal width 2a and the vertical width 2b of the trunk can be obtained as electric information (data) based on positional information of the cursor support portion 401 in the device main body 100. The trunk sectional area is calculated from the information relating to the horizontal width 2a and the vertical width 2b of the trunk obtained in such a way as described in the measurement principle of the visceral fat.

It should be noted that in the present embodiment, the visceral fat measuring device is provided with the measuring unit 400, and the vertical width and the horizontal width of the trunk and the trunk sectional area are automatically measured by this measuring unit 400. However, values obtained by other measurement devices or manual measurement and calculation can also be inputted into the device main body 100.

(Control Configuration of Visceral Fat Measuring Device)

Figure 4:
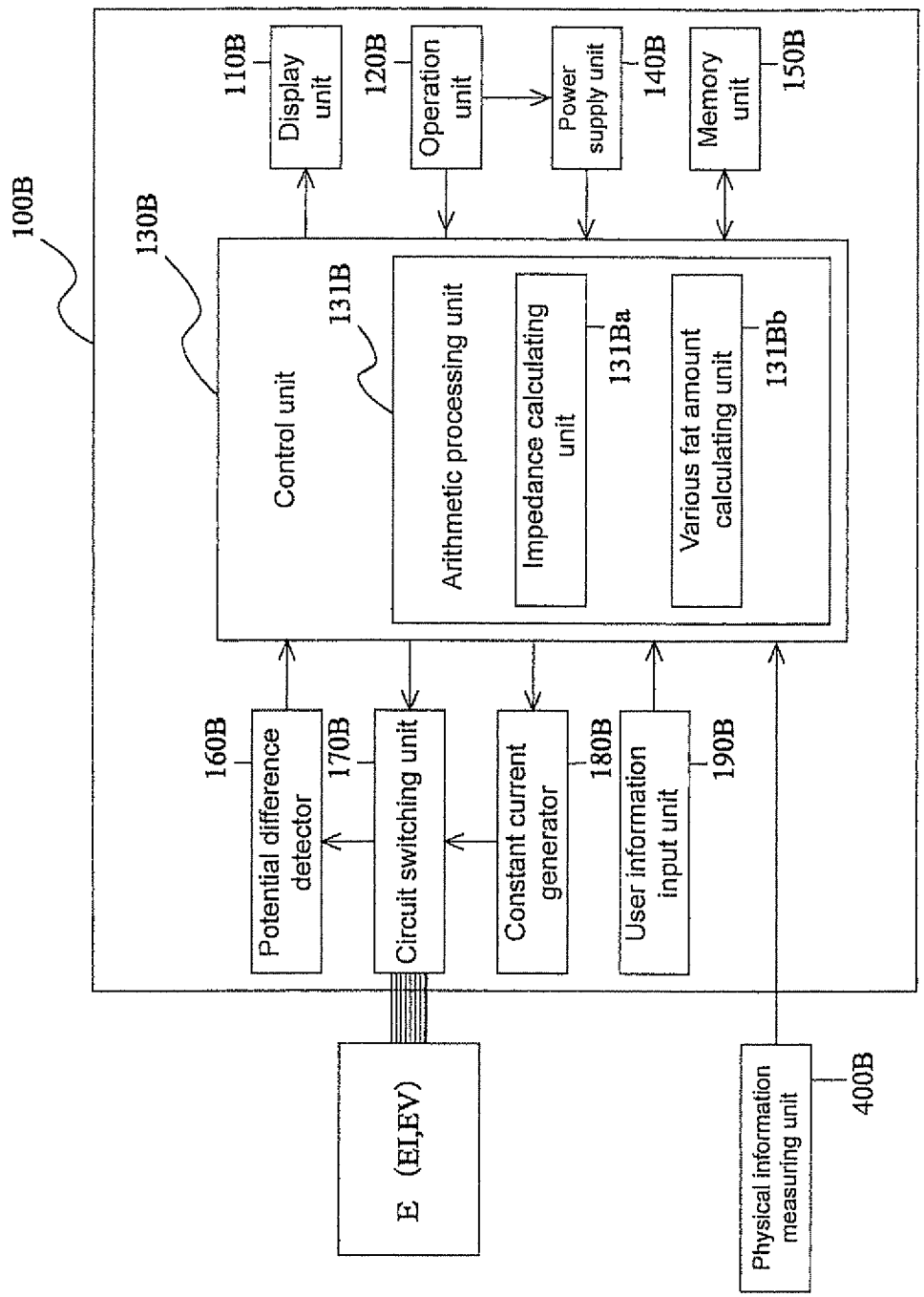
FIG. 4 is a control block diagram of the visceral fat measuring device according to the embodiment of the present invention.

A control configuration of the visceral fat measuring device according to the present embodiment will be described with reference to FIG. 4. FIG. 4 is a control block diagram of the visceral fat measuring device according to the embodiment of the present invention.

In the visceral fat measuring device according to the present embodiment, a device main body 100B is provided with a control unit (CPU) 130B, a display unit 110B, an operation unit 120B, a power supply unit 140B, a memory unit 150B, a potential difference detector 160B, a circuit switching unit 170B, a constant current generator 180B, and a user information input unit 190B.

The display unit 110B having a role of displaying input information from the operation unit 120B and the user information input unit 190B, the measurement result, and the like is formed by a liquid crystal display and the like. The operation unit 120B having a role of enabling the user or the like to input various information is formed by various buttons, a touchscreen, and the like. It should be noted that in the present embodiment, in addition to the input of the user information from the operation unit 120B, the user information is inputted from a barcode reader, a card reader, a USB memory, or the like via the user information input unit 190B.

The power supply unit 140B has a role of supplying the electric power to the control unit 130B and the like. When the power supply is turned on by the operation unit 120B, the electric power is supplied to the units, and when the power supply is turned off, the supply of the electric power is stopped. The memory unit 150B stores various data, programs, and the like for measuring the visceral fat.

The electrodes E respectively provided in the clips 201, 202, 203, 204 and the electrodes E provided in the belt are electrically connected to the circuit switching unit 170B provided in the device main body 100B. A physical information measuring unit 400B provided in the measuring unit 400 is electrically connected to the control unit 130B provided in the device main body 100B.

The control unit 130B has a role of controlling the entire visceral fat measuring device. The control unit 130B is provided with an arithmetic processing unit 131B. This arithmetic processing unit 131B is provided with an impedance calculating unit 131Ba for calculating impedance based on various information sent to the control unit 130B, and a various fat amount calculating unit 131Bb for calculating various fat amounts based on the calculated impedance.

The circuit switching unit 170B is for example formed by a plurality of relay circuits. This circuit switching unit 170B has a role of changing the electric circuit based on a command from the control unit 130B. That is, as described above, the circuit switching unit changes the electric circuit so as to have a circuit configuration shown in FIG. 1 in a case where the impedance information of the entire trunk is obtained, and to have a circuit configuration shown in FIG. 2 in a case where the impedance information of the surface layer of the trunk on the dorsal side is obtained.

The constant current generator 180B applies a high frequency current (of 50 kHz, 500 µA, for example) based on a command from the control unit 130B. More specifically, in a case of the electric circuit shown in FIG. 1, the electric current I10 is applied between the electrodes EILa10, EIRa10 and the electrodes EILb10, EIRb10. In a case of the electric circuit shown in FIG. 2, the electric currents I21, I22 are respectively applied between the electrode EIa21 and the electrode EIb21 and between the electrode EIa22 and the electrode EIb22.

The potential difference detector 160B detects a potential difference between predetermined electrodes while the electric current is applied by the constant current generator 180B. More specifically, in a case of the electric circuit shown in FIG. 1, the potential difference V11 is detected between the electrode EVa11 and the electrode EVb11, the potential difference V12 is detected between the electrode EVa12 and the electrode EVb12, the potential difference V13 is detected between the electrode EVa13 and the electrode EVb13, and the potential difference V14 is detected between the electrode EVa14 and the electrode EVb14. In a case of the electric circuit shown in FIG. 2, the potential difference V21 is detected between the electrode EVa21 and the electrode EVb21, and the potential difference V22 is detected between the electrode EVa22 and the electrode EVb22.

The potential difference information detected by the potential difference detector 160B is sent to the control unit 130B.

The physical information obtained by measurement by the measuring unit 400 is sent from the physical information measuring unit 400B to the control unit 130B of the device main body 100B. It should be noted that the physical information in the present embodiment is information relating to size of the horizontal width $2a$ and size of the vertical width $2b$ of the trunk.

In the arithmetic processing unit 131B in the control unit 130B, the impedance calculating unit 131Ba calculates the impedance Zt of the entire trunk and the impedance Zs of the surface layer of the trunk based on the potential difference information sent from the potential difference detector 160B. In the arithmetic processing unit 131B, the various fat amount calculating unit 131Bb calculates the various fat amounts (including the visceral fat sectional area) based on the calculated impedance Zt of the entire trunk and the impedance Zs of the surface layer of the trunk, the physical information sent from the physical information measuring unit 400B, and various information sent from the operation unit 120B and the user information input unit 190B.

Next, a measuring order in the visceral fat measuring device according to the present embodiment will be briefly described.

Firstly, the user subjected to the measurement of the visceral fat or a person who performs the measurement of the user turns on the power supply of the device main body 100 (100B) and inputs the user information. The vertical width and the horizontal width of the trunk of the user are measured by the measuring unit 400. Thereby, the information relating to the horizontal width $2a$ and the vertical width $2b$ of the trunk of the user is sent to the device main body 100 (100B). It should be noted that in the device main body 100 (100B), the trunk sectional area St ($=\alpha \times \pi \times a \times b$) is calculated based on the information. It should be noted that the value $\alpha$ is read from the memory unit 150B.

Next, the clips 201, 202, 203, 204 are attached to the hands and the legs of the user and the belt 300 is wound around the waist of the user. The measurement of the impedance is started.

In the present embodiment, firstly, the circuit switching unit 170B controls so as to have the electric circuit shown in FIG. 1. Thereby, the impedance Zt of the entire trunk is calculated by the impedance calculating unit 131Ba of the control unit 130B. The various fat amount calculating unit 131Bb calculates the lean body sectional area Sa ($=\beta \times a \times (1/Zt)$) from this calculated impedance Zt, the value a obtained by the measurement by the measuring unit 400, and the value $\beta$ stored in the memory unit 150B.

Next, the circuit switching unit 170B controls so as to have the electric circuit shown in FIG. 2. Thereby, the impedance Zs of the surface layer of the trunk is calculated by the impedance calculating unit 131Ba of the control unit 130B. The various fat amount calculating unit 131Bb calculates the subcutaneous fat sectional area Sb ($=\gamma \times a \times Zs$) from this calculated impedance Zs, the value a obtained by the measurement by the measuring unit 400, and the value γ stored in the memory unit 150B.

The control unit 130B calculates the visceral fat sectional area Sx (=St−Sa−Sb) from the trunk sectional area St, the lean body sectional area Sa, and the subcutaneous fat sectional area Sb obtained as described above by the arithmetic processing unit 131B, and displays the values of the visceral fat sectional area Sx and the like on the display unit 110 (110B) as the measurement result. It should be noted that although a case where the various fat amount calculating unit determines the visceral fat sectional area Sx with using Sx=St−Sa−Sb is described in this measuring order, the visceral fat sectional area Sx may be determined with using Sx=St−Sa−Sb+δ, Sx=St−F (Zt, Zs, a, b), or the like as described in the measurement principle of the visceral fat.

(Belt)

Figure 5:
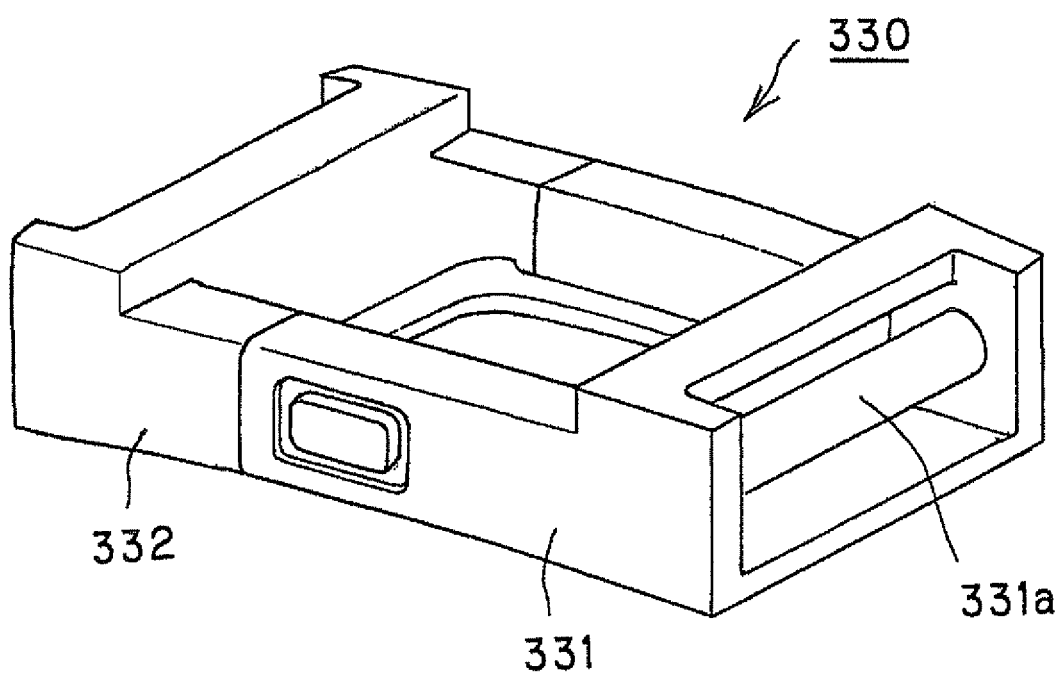
FIG. 5 is a perspective view of an outer appearance of a buckle in the visceral fat measuring device according to the embodiment of the present invention.
Figure 6:
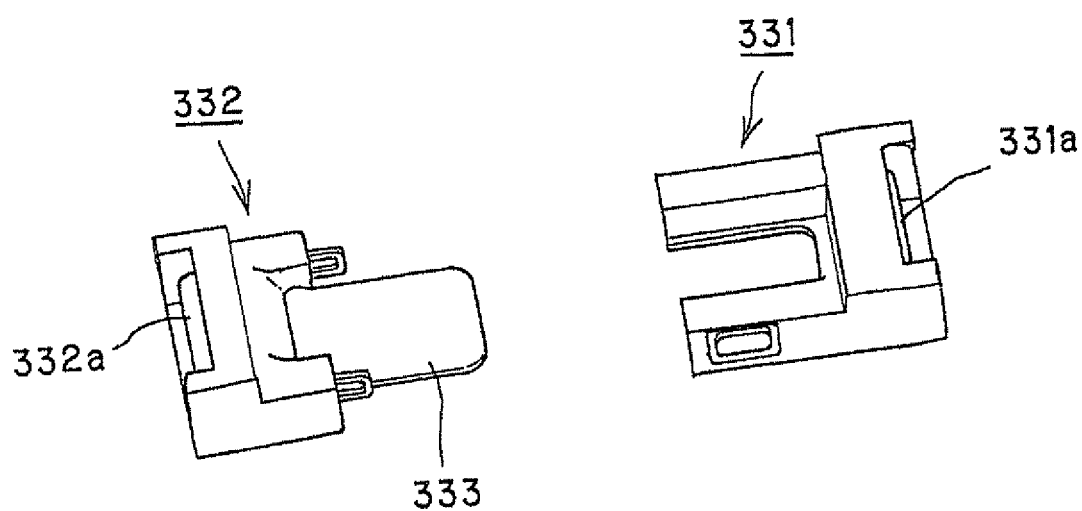
FIG. 6 is a perspective view showing a state that the buckle in the visceral fat measuring device according to the embodiment of the present invention is separated.
Figure 7:
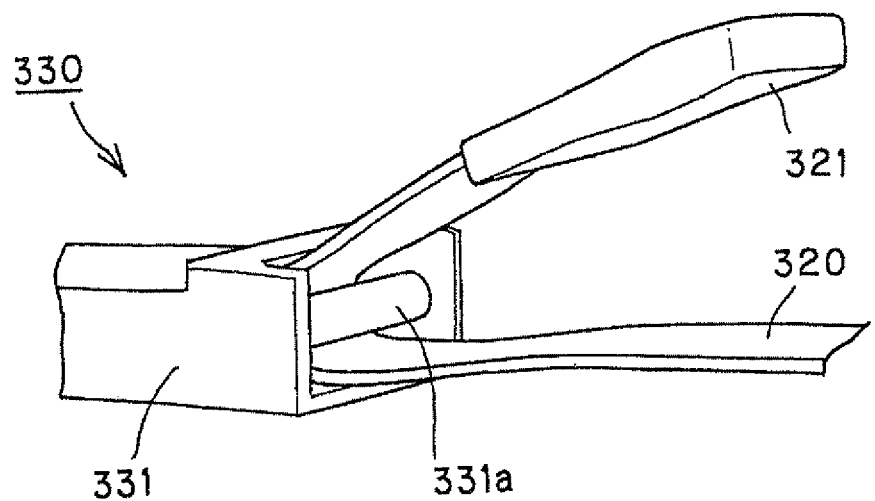
FIG. 7 is a perspective view showing a state that a belt portion is attached to the buckle in the visceral fat measuring device according to the embodiment of the present invention.
Figure 8:
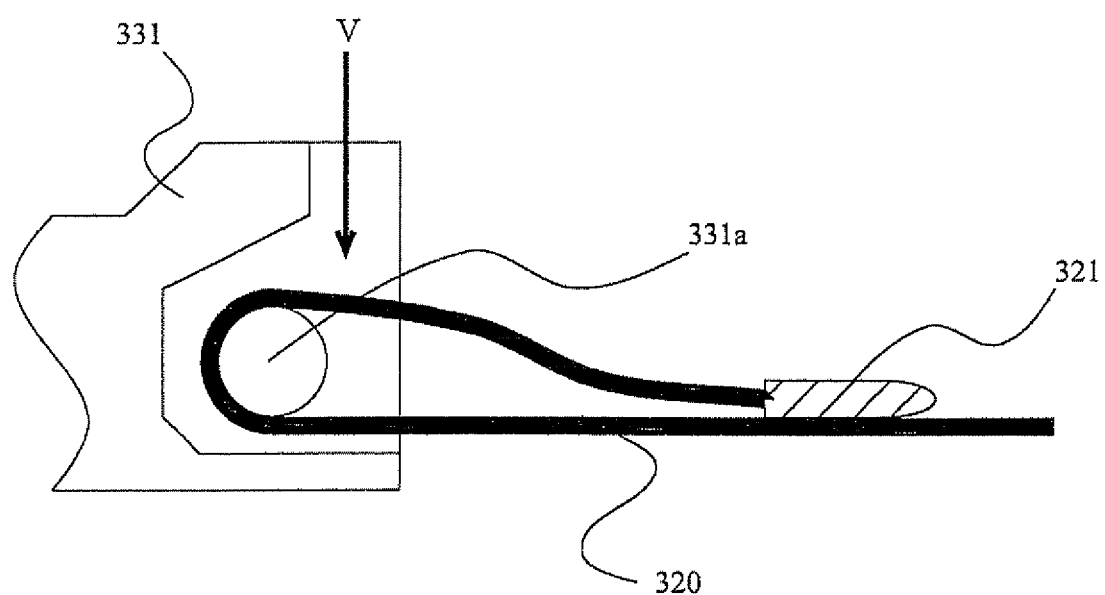
FIG. 8 is a schematic sectional view showing a state that a belt is fixed to the buckle in the visceral fat measuring device according to the embodiment of the present invention.
Figure 9:
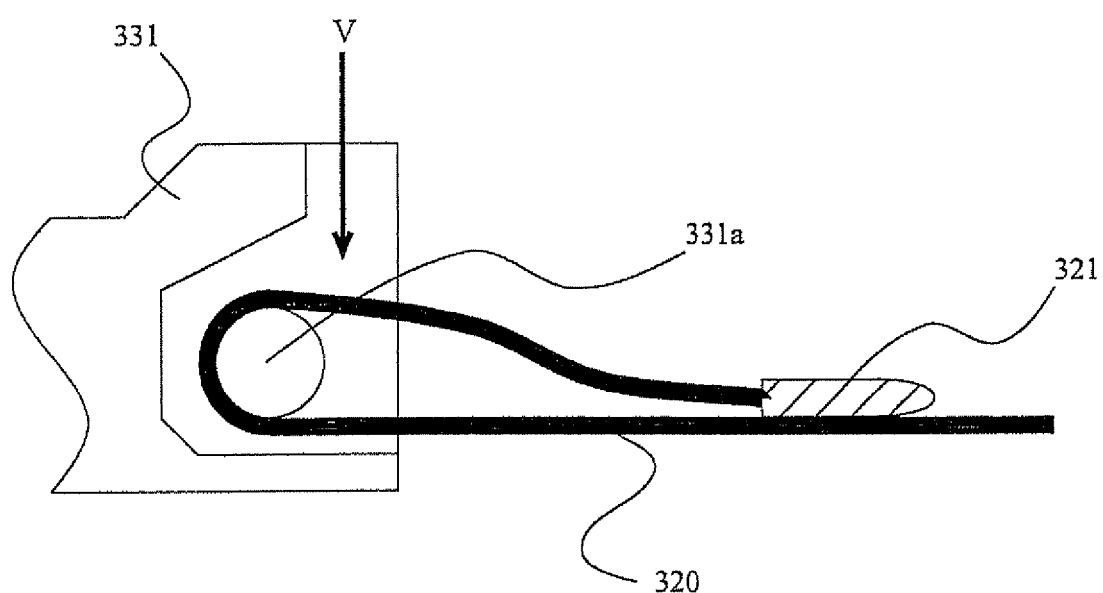
FIG. 9 is a schematic sectional view showing a state that the belt is fixed to the buckle in the visceral fat measuring device according to the embodiment of the present invention.
Figure 10:
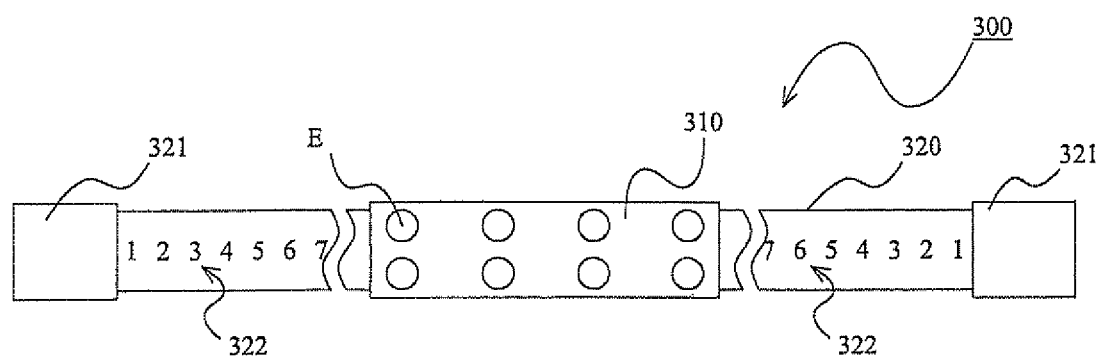
FIG. 10 is a partially broken plan view of the belt in the visceral fat measuring device according to the embodiment of the present invention.
Figure 11:
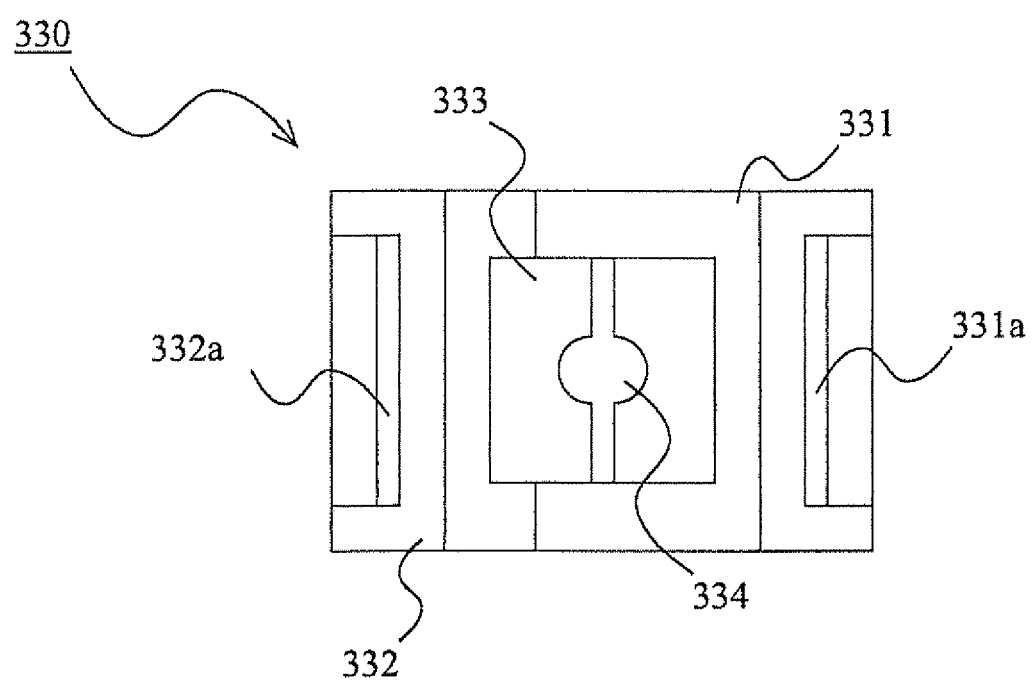
FIG. 11 is a plan view of the buckle in the visceral fat measuring device according to the embodiment of the present invention.
Figure 12:
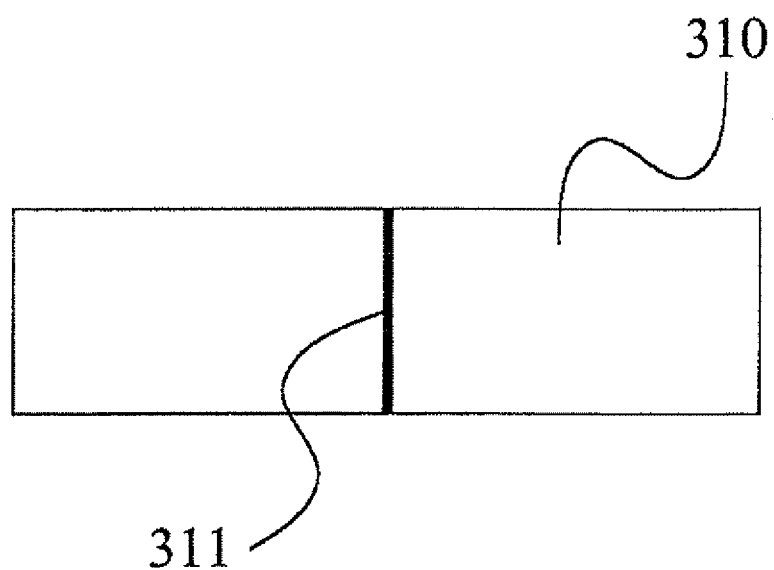
FIG. 12 is a back view of a pressing member in the visceral fat measuring device according to the embodiment of the present invention.

The belt 300 will be described further in detail with reference to FIGS. 5 to 12. FIG. 5 is a perspective view of an outer appearance of the buckle in the visceral fat measuring device according to the embodiment of the present invention. FIG. 6 is a perspective view showing a state that the buckle in the visceral fat measuring device according to the embodiment of the present invention is separated. FIG. 7 is a perspective view showing a state that the belt portion is attached to the buckle in the visceral fat measuring device according to the embodiment of the present invention. FIGS. 8 and 9 are schematic sectional views showing a state that the belt is fixed to the buckle in the visceral fat measuring device according to the embodiment of the present invention. FIG. 10 is a partially broken plan view of the belt in the visceral fat measuring device according to the embodiment of the present invention. FIG. 11 is a plan view of the buckle in the visceral fat measuring device according to the embodiment of the present invention. FIG. 12 is a back view of the pressing member in the visceral fat measuring device according to the embodiment of the present invention.

In the present embodiment, by winding the belt 300 around the waist so that the pressing member 310 is abutted against the slightly upper part of the coccyx as described above, the total of the eight electrodes E provided in the pressing member 310 are closely attached at the positions on the back side of the abdominal part on the dorsal of the user.

The pressing member 310 is formed so as to be symmetric. By performing the measurement in a state that a center in the width direction of the pressing member 310 is pressed onto the dorsal so as to be matched with a center in the width direction of the dorsal, the precise measurement can be performed.

In such a way, in order to precisely perform the measurement, there is a need for winding the belt 300 around the waist in a state that position matching of the pressing member 310 is performed so that the center in the width direction of the pressing member 310 is matched with the center in the width direction of the dorsal. However, in a case where the user subjected to the measurement himself/herself performs a task of winding the belt 300 around the waist, it is generally difficult to perform position matching of a member positioned on the dorsal side. Thus, in the belt 300 according to the present embodiment, various ideas are provided for easily performing the position matching of the pressing member 310. This will be described in detail.

The buckle 330 in the belt 300 according to the present embodiment is formed by a pair of members separable on the left and right sides (referred to as a first member 331 and a second member 332) as shown in FIG. 6. The first member 331 and the second member 332 are formed into different shapes from each other. However, the buckle 330 formed by connecting these is formed into a symmetrical shape.

This buckle 330 is provided with rollers 331a, 332a respectively in the vicinity of both left and right ends. A pair of the rollers 331a, 332a is to respectively support a pair of the belt portions 320.

In the present embodiment, surfaces of the belt portions 320 are formed by hook-and-loop fasteners. By pressing gripping portions 321 provided in front ends of the belt portions 320 onto the belt portions 320, the gripping portions 321 are fixed to the belt portions 320.

In a case where the belt 300 is wound around the waist and fixed, as shown in FIGS. 7 to 9, the gripping portion 321 is fixed to the belt portion 320 in a state that the front end of the belt portion 320 is brought from the lower side of the roller 331a (332a), wound around the roller 331a (332a) and pulled from the upper side. It should be noted that FIG. 8 shows a case of the user having relatively long waist length, and FIG. 9 shows a case of the user having relatively short waist length. In the present embodiment, since the surface of the belt portion 320 is formed by the hook-and-loop fastener as described above, the gripping portion 321 can be fixed at a free position.

In a case where the belt 300 is wound around the waist, there is a need for a task of respectively pulling the gripping portions 321 in the front ends of a pair of the belt portions 320 by both the hands in order to wind the belt 300 around the waist while performing the position matching of the pressing member 310 and the buckle 330. In this case, in the present embodiment, members for supporting the belt portions 320 are formed by the rollers 331a, 332a as described above. Thus, resistance at the time of moving the belt portions 320 relative to the buckle 330 is reduced, so that movement of the belt portions 320 relative to the buckle 330 is smoothly performed. Therefore, while performing the position matching of the pressing member 310 and the buckle 330, the task of winding the belt 300 around the waist can be smoothly performed. The gripping portions 321 can be fixed at the free positions as described above, and in addition, fine adjustment of the position matching can be easily performed.

In the present embodiment, indicators 322 showing distances from a reference position of the belt in the pressing member 310 are printed on a pair of the belt portions 320. In the present embodiment, the pressing member 310 is formed so as to be symmetric, and the indicators 322 can be indicators showing distances from a center position in the width direction of the pressing member 310. It should be noted that more specifically, in the present embodiment, numerals 1, 2, 3, . . . are printed at equal intervals in order from the sides of the gripping portions 321 as shown in FIG. 10. Therefore, at the time of winding the belt 300 around the waist, by setting the same numerals in a pair of the belt portions 320 respectively pulled out from the both sides of the buckle 330 to be seen around the vicinity of both ends of the buckle 330 (around parts shown by an arrow V in FIGS. 8 and 9), the pressing member 310 can be placed at a position right behind the buckle 330.

In the present embodiment, a bottom plate 333 of the buckle 330 is formed by a transparent plate so that the position matching of the buckle 330 is easily performed. Further, a slit 334 formed so that a center thereof has a substantially circular shape is provided in a center in the width direction of this bottom plate 333 so as to serve as an indicator showing a center in the width direction of the buckle 330. Thereby, by positioning the buckle 330 so that the navel is positioned in the substantially circular part of this slit 334, the position matching of the buckle 330 can be easily performed.

As described above, the buckle 330 is positioned so that the navel is positioned in the substantially circular part of the slit 334 provided in the bottom plate 333 of the buckle 330, and a pair of the belt portions 320 is pulled out so that the same numerals are seen around the vicinity of the both ends of the buckle 330. Thereby, the pressing member 310 can be positioned so that the center in the width direction of the pressing member 310 is matched with the center in the width direction of the dorsal.

In the present embodiment, as shown in FIG. 12, a slit 311 serving as an indicator showing the center position in the width direction of the pressing member 310 is provided on a back surface of a surface of the pressing member 310 to be pressed onto the dorsal. Thereby, in a case where a third person other than the user subjected to the measurement presses the pressing member 310 onto the dorsal of the user, the position matching of the pressing member 310 can be easily performed.

DESCRIPTION OF SYMBOLS 100, 100B: Device main body
110, 110B: Display unit
120, 120B: Operation unit
130B: Control unit
131B: Arithmetic processing unit
131Ba: Impedance calculating unit
131Bb: Various fat amount calculating unit
140B: Power supply unit
150B: Memory unit
160B: Potential difference detector
170B: Circuit switching unit
180B: Constant current generator
190B: User information input unit
201, 202, 203, 204: Clip
300: Belt
310: Pressing member
311: Slit
320: Belt portion
321: Gripping portion
322: Indicator
330: Buckle
331: First member
331a: Roller
332: Second member
332a: Roller
333: Bottom plate
334: Slit
400: Measuring unit
400B: Physical information measuring unit
401: Cursor support portion
401a: Horizontal width measuring cursor portion
401b: Vertical width measuring cursor portion
500: Socket
E: Electrode

The invention claimed is:

1. A visceral fat measuring device for calculating a visceral fat amount based on:
   trunk measurement information for use in obtaining an area of a cross-sectional plane of an abdominal part of a trunk which is orthogonal to a body axis of the trunk;
   impedance information of an entire trunk obtained by applying an electric current through the trunk from hands and legs and measuring a potential difference in part of a surface of the trunk; and
   impedance information of a surface layer of the trunk obtained by winding a belt having a plurality of electrodes around the trunk so as to apply the electric current through a vicinity of the surface layer of the trunk and measure a potential difference in part of the surface of the trunk,
   said visceral fat measuring device comprising a belt assembly that comprises:
   a pressing member to be placed on a dorsal side of a person subjected to measurement and provided with the electrodes;
   a first belt portion extending from a first side of the pressing member to a free end, said first belt portion being provided with first indicators showing a distance from the free end of the first belt portion;
   a second belt portion extending from a second side, opposite to said first side, of the pressing member to a free end, said second belt portion being provided with second indicators showing a distance from the free end of the second belt portion; and
   a buckle for connecting the first and second belt portions to one another, whereby
   the pressing member can be aligned by adjusting distances of the free ends of the first and second belt portions from the buckle based on the first and second indicators, said indicators being arranged along the first and second belt portions from the free ends towards the pressing member.

2. The visceral fat measuring device according to claim 1, comprising a potential difference detector for measuring the potential difference in part of a dorsal surface of the trunk.

3. The visceral fat measuring device according to claim 1, comprising a potential difference detector for measuring the potential difference in the body axis of the trunk.

4. The visceral fat measuring device according to claim 1, wherein the buckle is provided with a pair of rollers around which the first and second belt portions are respectively wound.

5. The visceral fat measuring device according to claim 1, wherein a transparent plate is provided in a center of the buckle, and an indicator showing a center in a width direction of the buckle is provided in the transparent plate.

6. The visceral fat measuring device according to claim 1, wherein an indicator is provided on a surface of the pressing member to show a center position between the first side and the second side of the pressing member.

7. The visceral fat measuring device according to claim 1, comprising a control unit configured to:
   calculate a lean body sectional area excluding fat from the impedance information of the entire trunk,
   calculate a subcutaneous fat sectional area from the impedance information of the surface layer of the trunk, and
   calculate a visceral fat sectional area by subtracting the lean body sectional area and the subcutaneous fat sectional area from the area of the cross-sectional plane obtained from the trunk measurement information.

8. The visceral fat measuring device according to claim 1, wherein:
   the first indicators include a plurality of first indicia periodically spaced apart and positioned along the first belt portion from the free end of the first belt portion to the pressing member; and
   the second indicators include a plurality of second indicia periodically spaced apart and positioned along the second belt portion from the free end of the second belt portion to the pressing member.

9. The visceral fat measuring device according to claim 8, wherein each of the first and second indicators includes a numerical series.

10. The visceral fat measuring device according to claim 9, wherein the numerical series of the first indicators is the same as the numerical series of the second indicators.

11. A belt assembly for use in a visceral fat measuring device for calculating a visceral fat amount, said belt assembly comprising:
   a pressing member to be placed on a dorsal side of a person subjected to measurement and provided with a plurality of electrodes;
   a first belt portion extending from a first side of the pressing member to a free end, said first belt portion being provided with first indicators showing a distance from the free end of the first belt portion;
   a second belt portion extending from a second side, opposite to said first side, of the pressing member to a free end, said second belt portion being provided with second indicators showing a distance from the free end of the second belt portion; and
   a buckle for connecting the first and second belt portions to one another, whereby
   the pressing member can be aligned by adjusting distances of the free ends of the first and second belt portions from the buckle based on the first and second indicators, said indicators being arranged along the first and second belt portions from the free ends towards the pressing member.

12. The belt assembly according to claim 11, wherein:
   the first indicators include a plurality of first indicia periodically spaced apart and positioned along the first belt portion from the free end of the first belt portion to the pressing member; and
   the second indicators include a plurality of second indicia periodically spaced apart and positioned along the second belt portion from the free end of the second belt portion to the pressing member.

13. The belt assembly according to claim 12, wherein each of the first and second indicators includes a numerical series.

14. The belt assembly according to claim 13, wherein the numerical series of the first indicators is the same as the numerical series of the second indicators.

15. A method of measuring an amount of visceral fat of a person using the visceral fat measuring device of claim 1, comprising:
   placing the belt assembly around the trunk of the person,
   aligning the pressing member on the dorsal side of the person by adjusting distances of the free ends of the first and second belt portions from the buckle,
   measuring impedance information of an entire trunk to calculate a lean body sectional area excluding fat,
   measuring impedance information of the surface layer of the trunk to calculate a subcutaneous fat sectional area, and
   calculating a visceral fat sectional area by subtracting the lean body sectional area and the subcutaneous fat sectional area from the area of the cross-sectional plane obtained from the trunk measurement information.

* * * * *